(12) United States Patent
Willemin et al.

(10) Patent No.: US 6,592,855 B1
(45) Date of Patent: Jul. 15, 2003

(54) USE OF A DIPHENYLDIMETHICONE DISSOLVED IN A NON-VOLATILE SILICONE SUCH AS PHENYLTRIMETHICONE FOR MAKING A COSMETIC OR PHARMACEUTICAL, IN PARTICULAR DERMATOLOGICAL, COMPOSITION COMPRISING A FATTY PHASE

(75) Inventors: Claudie Willemin, Paris (FR); Frédéric Burtin, Orleans (FR)

(73) Assignee: Parfums Christian Dior, Paris (FR)

( * ) Notice: Subject to any disclaimer, the term of this patent is extended or adjusted under 35 U.S.C. 154(b) by 0 days.

(21) Appl. No.: 09/555,731

(22) PCT Filed: Dec. 2, 1998

(86) PCT No.: PCT/FR98/02591

§ 371 (c)(1),
(2), (4) Date: Jun. 1, 2000

(87) PCT Pub. No.: WO99/27903

PCT Pub. Date: Jun. 10, 1999

(30) Foreign Application Priority Data

Dec. 2, 1997 (FR) ............................................ 97 15177

(51) Int. Cl.⁷ ................................................. A61K 7/06
(52) U.S. Cl. ........................ 424/70.1; 424/401; 424/59
(58) Field of Search .......................... 424/401, 59, 70.1

(56) References Cited

U.S. PATENT DOCUMENTS 5,804,169 A * 9/1998 Ramin .......................... 424/61
5,965,148 A * 10/1999 Agostini et al. ............. 424/401

FOREIGN PATENT DOCUMENTS

| EP | 756 864 A1 | 2/1997 |
| EP | 756 865 A1 | 2/1997 |
| WO | 97/12584 | 4/1997 |

* cited by examiner

*Primary Examiner*—Jose' G. Dees
*Assistant Examiner*—Konata M George
(74) *Attorney, Agent, or Firm*—Nath & Associates PLLC; Gary M. Nath; Jerald L. Meyer

(57) ABSTRACT

A novel silicone gum and the use of a silicone gum such as diphenyldimethicone dissolved in a silicone oil for making a cosmetic of pharmaceutical compositions, particularly dermatological compositions, containing a fatty phase. Anb exemplary silicone oil is phenyltrimethicone. Also contemplated is the preparation of a cosmetic or pharmaceutical composition for skin care, in particular for the face or the body or for hair care.

60 Claims, No Drawings

USE OF A DIPHENYLDIMETHICONE DISSOLVED IN A NON-VOLATILE SILICONE SUCH AS PHENYLTRIMETHICONE FOR MAKING A COSMETIC OR PHARMACEUTICAL, IN PARTICULAR DERMATOLOGICAL, COMPOSITION COMPRISING A FATTY PHASE

This application is a 371 of PCT/FR98/02591 filed Dec. 2, 1998.

The present invention essentially relates to the use of diphenyldimethicone gum dissolved in a non-volatile silicone of the phenyltrimethicone type for preparing a cosmetic or pharmaceutical composition, notably dermatological composition, comprising a fatty phase.

In the state of the prior art, it is known from the document WO 97/12584 of silicone compositions as well as their method of preparation and their use in cosmetics for treating the skin or the hair.

Within the context of the prior art, these silicone gums are dissolved in a volatile silicone oil and are, for example, available on the market under the commercial denomination MIRASIL® C-DPDM, from RHONE-POULENC, France, i.e. a diphenyldimethicone, dissolved in cyclomethicone.

The silicone gums are particularly useful in cosmetics, since they bring about qualities which are essentially sought after in cosmetics such as smoothness, a slippery power, a shininess, a filmogenic character, an effect of resistance to water, a waterproof effect, an adherence effect, a conditioning effect, an anti-static effect, a softening effect conferring a soft feel, and a substantive effect, and a good hold with time.

A main aim of the invention is to provide a solution which enables facilitating the incorporation of silicone gum in cosmetic compositions or even pharmaceutical compositions, notably dermatological compositions, comprising a fatty phase.

A further main aim of the invention is to provide a solution which enables making an easy incorporation of a silicone gum in cosmetic or pharmaceutical compositions, notably dermatological compositions, by increasing the possibilities of formulation of these products with an upkeep or preferably an improvement of the compatibility with the other ingredients of the fatty phase and particularly the fatty bodies such as the oils by the waxes, in thus obtaining products of very good quality.

The present invention provides for the first time a solution to the whole of the technical problems set forth above in a particularly simple manner, which is inexpensive, which can be used on a cosmetically, pharmaceutically or notably dermatologically industrial scale.

Thus, according to a first aspect, the present invention relates to the use of a silicone gum of the diphenyldimethicone type dissolved in a non-volatile silicone oil of the phenyltrimethicone type for preparing a cosmetic or pharmaceutical composition, notably dermatological composition, comprising a fatty phase.

Within the context of the invention, the silicone gum of the diphenyldimethicone type has the following formula (I):

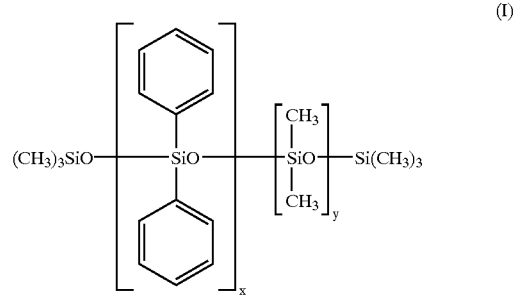

in which x represents the number of recurring units which is generally not very high, preferably less than about 500, advantageously between about 50 and about 150, even better between about 80 and about 120, while y represents the number of recurring units which is generally higher, preferably at least equal to 1,000 and even better between about 1,000 and about 2,000.

Furthermore, within the context of the invention, non-volatile solubilising silicone oil of the silicone gum is a phenyltrimethicone of formula (II) below:

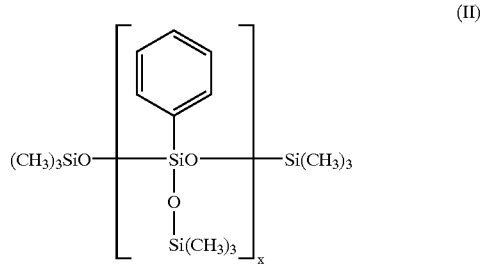

in which x represents the number of recurring units which enables a viscosity to be obtained between about 10 and about 40 centistokes at a temperature of 25° C. Preferably, x will have an average value of between 2 and 3.

Within the context of the invention, the relative proportion between the diphenyldimethicone silicone gum and the solubilising phenyltrimethicone silicone oil can vary within wide limits. However, this relative proportion will advantageously be between 0.1 to about 20% by weight of silicone gum, with respect to the mixture of silicone gum and solubilising phenyltrimethicone silicone oil, and even better between about 5 and about 15 by weight and ideally about 15% by weight.

However, according to other embodiments of the invention, the binary mixture of silicone gum of the dimethicone type and solubilising silicone oil of the phenyltrimethicone type will only constitute a part of the fatty phase, advantageously of 0.1 to 100%, better of 1% to 75%, even better 5 to 50% of the fatty phase.

Thus, within the context of the invention, the fatty phase can be constituted entirely of the binary mixture of the silicone gum mentioned above dissolved in the silicone oil of the phenyltrimethicone type.

This fatty phase will advantageously comprise at least one other silicone oil or non-silicone oil and optionally a fatty body which can advantageously be of plant origin.

At least one ester of glycerol and fatty acid in the form of a mono-, di- or tri-glyceride, an ester of acid and alcohol, the acid and/or alcohol being fatty, can be used as non-silicone oil, more generally a non-silicone fatty body.

Within the context of the present invention, i.e. of the description and the claims, the expression <<fatty acid>> is understood as meaning an acid having in general from 5 to 30 carbon atoms, having a linear or branched chain or even cyclic chain, which is saturated or unsaturated, which can comprise one or more aromatic rings, particularly one or more phenyl or benzyl groups.

Furthermore, within the context of the invention, i.e. of the description and the claims, it is also understood that the expression <<fatty alcohol>>, means an alcohol having at least 8 carbon atoms, preferably between 8 and 30 carbon atoms.

Within the context of the invention, the fatty acid can also be used alone, having in this case a higher number of carbon atoms, particularly at least 12 carbon atoms, as defined above, and within the context of the use of a fatty alcohol alone, also having in this case at least 12 carbon atoms, as defined above.

Surfactant or emulsifying agents of the ionic or non-ionic type, such as sorbitan esters, polyoxyethylenated fatty alcohols, sucrose esters, can also be incorporated in the cosmetic or pharmaceutical compositions, notably dermatological compositions, of the invention.

According to an advantageous embodiment of the invention, the cosmetic or pharmaceutical compositions, notably dermatological compositions, can also contain at least one cosmetically or pharmaceutically acceptable additive, notably dermatologically acceptable additive, such as a thickening agent, a fatty acid ester particularly esters of fatty acid and glycerol, other volatile or non-volatile silicone oils, solar filters, plant oils, synthetic oils, perfumes, preservatives.

The compositions according to the invention can be formulated in various forms which are well known to the person skilled in the art, such as gel, milk, cream, lotion of variable consistency adapted to the uses sought after.

Within the context of the invention, the cosmetic or pharmaceutical compositions, notably dermatological compositions, will more particularly be used in the field of care of the skin, particularly of the face or of the body.

According to another variant, the cosmetic or pharmaceutical compositions, notably dermatological compositions, according to the invention, can be used for hair care.

According to a second aspect, the present invention also covers cosmetic, pharmaceutical compositions, notably dermatological compositions, characterised in that they comprise a fatty phase comprising a silicone gum of the diphenyldimethicone type dissolved in a non-volatile silicone oil of the phenyltrimethicone type, particularly as defined above.

According to an advantageous embodiment of the invention, this composition is a composition for the care of the skin and further comprises in the fatty phase a compound selected from the group consisting of:

an ester of glycerol, advantageously a triglyceride which is liquid at ambient temperature, such as glycerol tricaprylate/caprate, a caprylic/capric/succinic acid triglyceride, particularly at a concentration of about 1 to about 10% by weight, a silicone oil of the phenyltrimethicone or dimethicone type particularly at a concentration between about 1 and about 10% by weight, better of the order of 2 to 5% by weight, a plant oil, advantageously a jojoba oil or a meadowfoam seed oil, particularly at a concentration of 0.5 to 10% by weight, better of about 1 to about 5% by weight, at least one gelling agent, advantageously a polysaccharide such as a xanthan gum or an acrylic polymer of the carbomer type, or a gelling mixture based on isoparaffin, polyacrylamide and polyoxyethylenated lauric alcohol, particularly commercially available under the commercial denomination of SEPIGEL 305 marketed by the company SEPPIC, particularly at a concentration between about 0.1 and about 10% by weight, better between about 0.1 and about 5% by weight, an emulsifying/surfactant agent of the non-ionic type such as sorbitan stearate or a polyoxyethylenated sorbitan stearate or a sucrose ester such as sucrose stearate, particularly at a concentration between about 0.5 and about 5% by weight.

According to another embodiment of the invention, within the context of a composition intended for solar protection, this composition further comprises the following ingredients:

at least one chemical solar filter such as octyl methoxycinnamate, butylmethoxydibenzoylmethane, benzophenone-3 and benzophenone-4.

In the case of the use of octyl methoxycinnamate, a concentration between 0.1 and 10% by weight will in particular be used, in the case of butylmethoxydibenzoylmethane, a concentration advantageously between 0.1 and 5% by weight will be used, particularly of the order of 2 to 3% by weight, and for benzophenone-3 or -4, a concentration between 0.1 and 5% by weight will be used in particular, at least one physical solar filter such as micronised titanium oxide particularly at a concentration between 0.1 and 20% by weight; micronised zinc oxide particularly at a concentration between 0.1 and 20% by weight, or any hybrid particles made from a mixture of titanium oxide or zinc oxide with another component particularly when these oxides are fixed on the surface of a polymeric particle, for example particles of polyethylene or of polypropylene comprising such oxides on their surface.

Such cosmetic, pharmaceutical compositions, notably dermatological compositions, can for example be constituted by hair compositions, in any form whatsoever, for example gel or cream, compositions intended for application on the skin, topically, in the form of an emulsion of the water-in-oil type or oil-in-water type, in the form of a gel, particularly a transparent gel, or even a lotion, or even anhydrous solid forms such as rods or sticks, or even products for the nails.

According to a second aspect, the present invention also relates to cosmetic or pharmaceutical compositions, notably dermatological compositions, comprising a fatty phase which itself comprises a mixture of silicone gum of the diphenyldimethicone type dissolved in a silicone oil of the phenyltrimethicone type, more particularly as defined above.

Naturally, these cosmetic or pharmaceutical compositions, notably dermatological compositions, can contain other active ingredients that the person skilled in the art will desire to incorporate, as well as various cosmetically, pharmaceutically, or dermatologically acceptable excipients or vehicles which are well-known to the person skilled in the art.

Other aims, characteristics and advantages of the invention will also appear clearly from the following description which is made in relation with various currently preferred preparation examples of the invention, which are given solely as an illustration and which will in no way limit the scope of the invention.

In the Examples, the proportions are given by weight, the temperature is ambient temperature, and the pressure is atmospheric pressure, unless indicated otherwise.

EXAMPLE 1 OF THE INVENTION

Cosmetic Composition According to the Invention of Makeup of the Lipstick Type

This composition is formulated from the following ingredients:

| | |
|---|---|
| binary composition of diphenyldimethicone silicone gum dissolved in a trimethicone silicone oil, the silicone gum representing 15% of the mixture | 5% |
| isostearyl isostearate | 20% |
| octyl palmitate | 10% |
| microcrystalline wax | 8% |
| candelilla wax | 5% |
| beeswax | 5% |
| glycerol tricaprylate/caprate | 4% |
| octyl methoxy cinnamate | 3% |
| cetyl ricinoleate | 3% |
| iron oxides | 5% |
| organic pigments on lacquers | 1.5% |
| pearlescents | 6% |
| perfume | 0.3% |
| castor oil with preservative | qsp 100% |

This cosmetic composition is prepared in the following manner:

All the fatty components including the binary composition of the invention, with the exception of the pigments and pearlescents, are incorporated, which are mixed while heating to a temperature of 85–90° C. in order to melt the substances which are solid at ambient temperature, such as the waxes, until a complete homogeneity is obtained.

The pigments and pearlescents are then added which are dispersed beforehand in a part of castor oil until perfect homogeneity is obtained. The composition is then poured in the hot into moulds which enables giving the final shape of the lipsticks and which are left to cool before being turned out, in a manner well-known to the person skilled in the art.

EXAMPLE 2 ACCORDING TO THE INVENTION

Cosmetic Composition According to the Invention of Makeup of the Lipstick Type

This composition is formulated from the following ingredients:

| | |
|---|---|
| binary composition of Example 1 | 10% |
| isostearyl isostearate | 20% |
| octyl palmitate | 10% |
| microcrystalline wax | 8% |
| candelilla wax | 5% |
| beeswax | 5% |
| glycerol tricaprylate/caprate | 4% |
| octyl methoxy cinnamate | 3% |
| cetyl ricinoleate | 3% |
| iron oxides | 5% |
| organic pigments on lacquers | 1.5% |
| pearlescents | 6% |
| perfume | 0.3% |
| castor oil with preservative | qsp 100% |

This composition is prepared as in Example 1.

EXAMPLE 3 ACCORDING TO THE INVENTION

Cosmetic Composition According to the Invention of Makeup of the Powder Compact Type This composition is formulated from the following ingredients:

| | |
|---|---|
| binary composition of Example 1 | 1.5% |
| nylon-12 | 6% |
| calcium stearate | 2% |
| octyl palmitate | 1% |
| cetostearyl octanoate | 0.5% |
| silicone treated mica | 15% |
| preservatives such as methyl, propyl or butyl parahydroxybenzoate | 0.25% |
| anti-oxidising agents such as propyl gallate | 0.2% |
| mica | qsp 100% |

This composition is prepared by mixing the whole of the components in a mixer adapted to the preparation of powder, and by compacting in a classical compacting device used in cosmetics for obtaining a powder compact.

EXAMPLE 4 ACCORDING TO THE INVENTION

Cosmetic Composition in the Form of a Water in Silicone Foundation

| | |
|---|---|
| I - Fatty phase | |
| binary composition of Example 1 | 5% |
| laurylmethicone copolyol | 3.5% |
| cyclomethicone | 15% |
| octyldodecylstearoylstearate | 5% |
| silicone treated pigment such as iron oxides | 8% |
| II - Aqueous phase | |
| sodium chloride | 2% |
| glycerine | 3% |
| preservatives such as methyl parahydroxybenzoate | 0.15% |
| modified starch | 4% |
| nylon-12 | 4% |
| water | qsp 100% |

This composition is prepared in the following manner:

The components of the fatty phase are first of all mixed with stirring until a complete homogeneity is obtained. Independently, all the components of the aqueous phase are mixed with the water until complete homogeneity.

The aqueous phase and the fatty phase are then mixed with vigorous and progressive stirring until a homogeneous emulsion is obtained.

A cosmetic foundation composition is thus obtained comprising silicones and which has a good substantivity, a good hold on the skin, a good resistance to water and a good resistance to perspiration.

What is claimed is:

1. A method of cosmetic care comprising applying to skin zones in need thereof a cosmetic composition comprising a fatty phase comprising a diphenyldimethicone silicone gum dissolved in a phenyltrimethicone non-volatile silicone oil, the diphenyldimethicone having the following formula (I):

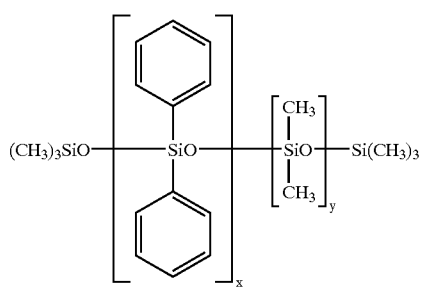

in which x represents the number of recurring units which is less than about 500 while y represents the number of recurring units which is at least equal to 1,000.

2. The method of claim 1, wherein x represents the number of recurring units which is ranging between about 50 and about 150 while y represents the number of recurring units which is ranging between 1,000 and about 2,000.

3. The method of claim 1, wherein x represents the number of recurring units which is ranging about 80 and 120 while y represents the number of recurring units ranging between 1,000 and about 2,000.

4. The method of claim 1, wherein the non-volatile solubilising silicone oil of the silicone is gum is a phenyltrimethicone of the following formula (II):

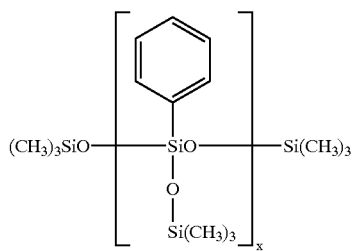

in which x represents the number of recurring units which provides a viscosity between about 10 and about 40 centiStokes at a temperature of 25° C.

5. The method of claim 4, wherein x has an average value ranging between 2 and 3.

6. The method of claim 1, wherein the fatty phase is constituted substantially entirely of the mixture of the diphenyldimethicone silicone gum dissolved in the phenyltrimethicone non-volatile silicone oil.

7. The method of claim 1, wherein the mixture of the phenyltrimethicone silicone oil and of the phenyltrimethicone non-volatile silicone oil constitutes 0.1 to 100 weight % of the fatty phase.

8. The method of claim 1, wherein the mixture of the phenyltrimethicone silicone oil and of the phenyltrimethicone non-volatile silicone oil constitutes 1 to 75 weight % of the fatty phase.

9. The method of claim 1, wherein the mixture of the phenyltrimethicone silicone oil and of the phenyltrimethicone non-volatile silicone oil constitutes 5 to 50 weight % of the fatty phase.

10. The method of claim 1, wherein the relative proportion is between 0.1 and about 20% by weight of diphenyldimethicone silicone gum with respect to the mixture of silicone gum and of solubilising phenyltrimethicone silicone oil.

11. The method of claim 1, wherein the relative proportion is between about 5 and about 15% by weight of diphenyldimethicone silicone gum with respect to the mixture of silicone gum and of solubilising phenyltrimethicone silicone oil.

12. The method of claim 1, wherein the relative proportion is about 15% by weight of diphenyldimethicone silicone gum with respect to the mixture of silicone gum and solubilising phenyltrimethicone silicone oil.

13. The method of claim 1, wherein the fatty phase comprises at least one further oil selected from a further silicone oil and a further non-silicone oil.

14. The method of claim 1, wherein the cosmetic composition further comprises at least one cosmetically acceptable additive selected from the group consisting of a thickening agent, a fatty acid ester of a fatty acid and glycerol, a further volatile silicone oil, a further non-volatile silicone oil, a solar filter, a plant oil, a synthetic oil, a perfume, a preservative and any mixtures thereof.

15. The method of claim 13, wherein the further non-silicone oil is selected from the group consisting of at least one ester of glycerol and a fatty acid, an ester of a fatty acid and an alcohol, an ester of an acid and a fatty alcohol, and an ester of a fatty acid and a fatty alcohol.

16. The method of claim 1, further comprising at least one surfactant selected from the group consisting of a sorbitan ester, a polyoxyethylenated fatty alcohol, and a sucrose ester.

17. The method of claim 1, which is a method for hair care.

18. The method of claim 1, which is a method of care of the face skin or of the body skin.

19. A method of pharmaceutical treatment comprising applying to skin zones in need thereof of a pharmaceutical composition comprising a fatty phase comprising a diphenyldimethicone silicone gum dissolved in a phenyltrimethicone non-volatile silicone oil, the diphenyldimethicone having the following formula (I):

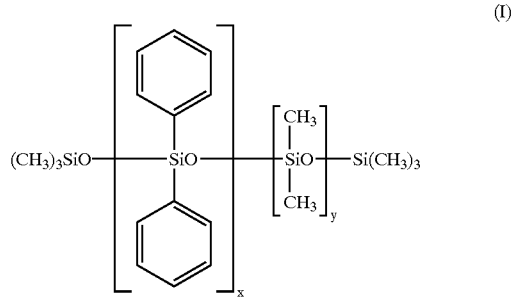

in which x represents the number of recurring units which is less than about 500 while y represents the number of recurring units which is at least equal to 1,000.

20. The method of claim 19, wherein x represents the number of recurring units which is ranging between about 50 and about 150 while y represents the number of recurring units which is ranging between 1,000 and about 2,000.

21. The method of claim 19, wherein x represents the number of recurring units which is ranging between about 80 and about 120 while y represents the number of recurring units ranging between 1,000 and about 2,000.

22. The method of claim 19, wherein the non-volatile solubilising silicone oil of the silicone gum is a phenyltrimethicone of the following formula (II):

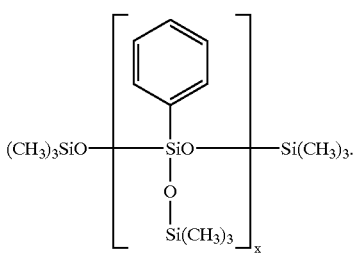

in which x represents the number of recurring units which provides a viscosity between about 10 and about 40 centiStokes at a temperature of 25° C.

23. The method of claim 18, wherein x has an average value ranging between 2 and 3.

24. The method of claim 19, the fatty phase is constituted substantially entirely of the mixture of the diphenyldimethicone silicone gum dissolved in the phenyltrimethicone non-volatile silicone oil.

25. The method of claim 19, wherein the mixture of the phenyltrimethicone silicone oil and of the phenyltrimethicone non-volatile silicone oil constitutes 0.1 to 100 weight % of the fatty phase.

26. The method of claim 19, wherein the mixture of the phenyltrimethicone silicone oil and of the phenyltrimethicone non-volatile silicone oil constitutes 1 to 75 weight % of the fatty phase.

27. The method of claim 19, wherein the mixture of the phenyltrimethicone silicone oil and of the phenyltrimethicone non-volatile silicone oil constitutes 5 to 50 weight % of the fatty phase.

28. The method of claim 19, wherein the relative proportion is between 0.1 to about 20% by weight of diphenyldimethicone silicone gum with respect to the mixture of silicone gum and of solubilising phenyltrimethicone silicone oil.

29. The method of claim 19, wherein the relative proportion is between about 5 to about 15% by weight of diphenyldimethicone silicone gum with respect to the mixture of silicone gum and of solubilising phenyltrimethicone silicone oil.

30. The method of claim 19, wherein the relative proportion is about 15% by weight of diphenyldimethicone silicone gum with respect to the mixture of a silicone gum and solubilising phenyltrimethicone silicone oil.

31. The method of claim 19, wherein the pharmaceutical composition further comprises at least one pharmaceutically acceptable additive selected from the group consisting of a thickening agent, fatty acid ester of a fatty acid and glycerol, a further volatile silicone oil, a further non-volatile silicone oil, a solar filter, a plant oil, a synthetic oil, a perfume, a preservative, in any mixture thereof.

32. A cosmetic composition having a fatty phase comprising diphenyldimethicone silicone gum dissolved in a non-volatile phenyltrimethicone silicone oil, the diphenyldimethicone having the following formula (I):

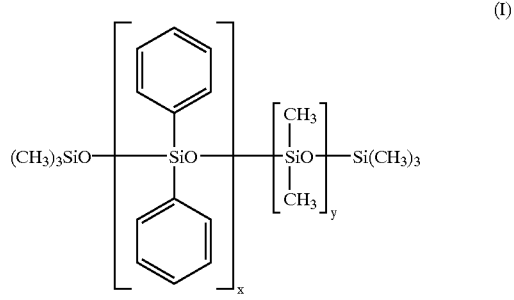

in which x represents the number of recurring units which is less than about 500 while y represents the number of recurring units which is at least equal to 1,000, and wherein the non-volatile solubilizing silicone oil of the silicone gum is a phenyltrimethicone of the following formula (II):

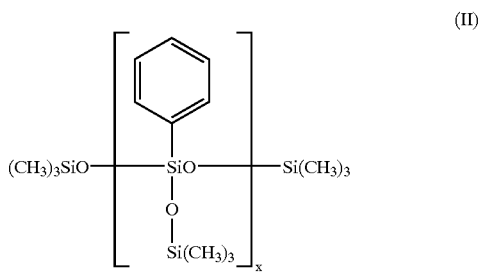

in which x represents the number of recurring units which provides a viscosity between about 10 and about 40 centistokes at a temperature of 25° C.

33. The composition of claim 32, wherein x represents the number of recurring units which is ranging between about 50 and about 150 while y represents the number of recurring units which is ranging between 1,000 and about 2,000.

34. The composition of claim 32, wherein x represents the number of recurring units which is ranging between about 80 and about 120 while y represents the number of recurring units ranging between 1,000 and about 2,000.

35. The composition of claim 32, wherein x has an average value ranging between 2 and 3.

36. A cosmetic composition having a fatty phase comprising diphenyldimethicone silicone gum dissolved in a non-volatile phenyltrimethicone silicone oil, the diphenyldimethicone having the following formula (I):

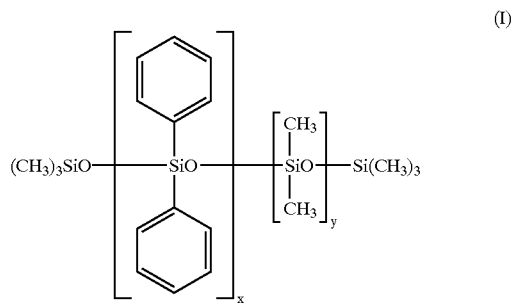

in which x represents the number of recurring units which is less than about 500 while y represents the number of recurring units which is at least equal to 1,000, wherein the fatty phase consists essentially of the mixture of the diphenyldimethicone silicone gum dissolved in the phenyltrimethicone non-volatile silicone oil.

37. The composition of claim 32, wherein the mixture of the phenyltrimethicone silicone oil and of the phenyltrimethicone non-volatile silicone oil constitutes 0.1 to 100 weight % of the fatty phase.

38. The composition of claim 32, wherein the mixture of the phenyltrimethicone silicone oil and of the phenyltrimethicone non-volatile silicone oil constitutes 1 to 75 weight % of the fatty phase.

39. The composition of claim 32, wherein the mixture of the phenyltrimethicone silicone oil and of the phenyltrimethicone non-volatile silicone oil constitutes 5 to 50 weight % of the fatty phase.

40. The composition of claim 32, wherein the relative proportion is between 0.1 to about 20% by weight of diphenyldimethicone silicone gum with respect to the mixture of silicone gum and of solubilising phenyltrimethicone silicone oil.

41. The composition of claim 32, wherein the relative proportion is between about 5 to about 15% by weight of diphenyldimethicone silicone gum with respect to the mixture of silicone gum and of solubilising phenyltrimethicone silicone oil.

42. The composition of claim 32, the relative proportion is about 15% by weight of diphenyldimethicone silicone gum width respect to the mixture of a silicone gum and solubilising phenyltrimethicone silicone oil.

43. A cosmetic composition having a fatty phase comprising diphenyldimethicone silicone gum dissolved in a non-volatile phenyltrimethicone silicone oil, the diphenyldimethicone having the following formula (I):

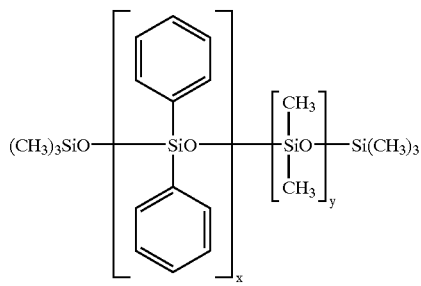

in which x represents the number of recurring units which is less than about 500 while y represents the number of recurring units which is at least equal to 1,000, wherein the fatty phase comprises at least one further oil selected from a further silicone oil and a further non-silicone oil.

44. The composition of claim 43, wherein the further non-silicone oil is selected from the group consisting of at least one ester of glycerol and a fatty acid, an ester of a fatty acid and an alcohol, an ester of an acid and a fatty alcohol, and an ester of a fatty acid and a fatty alcohol.

45. The composition of claim 32, further comprising at least one surfactant selected from the group consisting of a sorbitan ester, a polyoxyethylenated fatty alcohol, and a sucrose ester.

46. A cosmetic composition having a fatty phase comprising diphenyldimethicone silicone gum dissolved in a non-volatile phenyltrimethicone silicone oil, the diphenyldimethicone having the following formula (I):

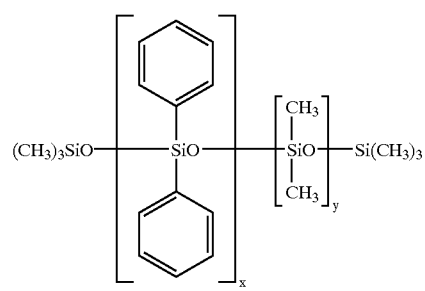

in which x represents the number of recurring units which is less than about 500 while y represents the number of recurring units which is at least equal to 1,000, wherein said diphenyldimethicone silicone gum dissolved in a non-volatile phenyltrimethicone silicone oil is present at a concentration between about 1 and about 10% by weight in the fatty phase; and at least one compound selected from the group consisting of an ester of glycerol at a concentration of about 1 to about 10% by weight; a plant oil at a concentration of 0.5 to 10% by weight; at least one gelling agent at a concentration between about 0.1 and about 5% by weight; and a surfactant at a concentration ranging between about 0.5 and about 5% by weight.

47. The composition of claim 46, wherein said ester of glycerol is selected from the group consisting of a glycerol tricaprylate, a glycerol caprate, a glycerol tricaprylate/caprate mixture, a caprylic/capric/succinic acid triglyceride; said plant oil is selected from jojoba oil and meadow foam seed oil, said gelling agent is selected from the group consisting of a polysaccharide, an acrylic polymer of the carbomer family; an isoparaffin, a polyacrylamide and polyoxyethylenated lauric alcohol; said surfactant is selected from the group consisting of a sorbitan, sorbitan stearate, a polyoxyethylenated sorbitan stearate, a sucrose ester, and sucrose stearate.

48. The composition of claim 32, further comprising a solar filter at a concentration ranging between 0.1 and 10% by weight of the composition.

49. The composition of claim 48, wherein said solar filter is selected from the group consisting of octyl methoxycinnamate, butylmethoxydibenzoylmethane, benzophenone-3 and benzophenone-4.

50. The composition of claim 48, wherein said solar filter is selected from the group consisting of micronised titanium oxide, micronised zinc oxide hybrid particles resulting from titanium oxide coated on the surface of a polymeric particle.

51. The composition of claim 50, wherein said polymeric particle is selected from the group consisting of polyethylene and polypropylene.

52. A pharmaceutical composition comprising a fatty phase comprising a diphenyldimethicone silicone gum dissolved in a non-volatile phenyltrimethicone silicone oil, the diphenyldimethicone has the following formula (I):

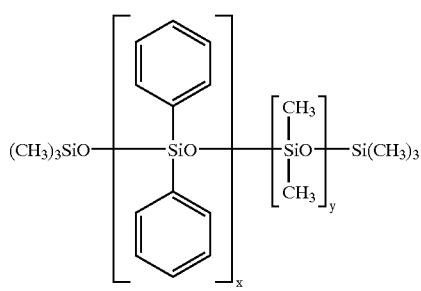

in which x represents the number of recurring units which is less than about 500 while y represents the number of recurring units which is at least equal to 1,000.

53. The pharmaceutical composition of claim 52, wherein the fatty phase is constituted substantially entirely of the mixture of the diphenyldimethicone silicone gum dissolved in the silicone oil of phenyltrimethicone.

54. The pharmaceutical composition of claim 52, wherein the mixture of dimethicone silicone gum and of solubilising silicone oil of phenyltrimethicone represents by weight from 1% to 75% of the fatty phase.

55. The composition of claim 52, wherein the diphenyldimethicone silicone gum represents between 0.1 and about 20% by weight of the mixture of silicone gum and solubilising phenyltrimethicone silicone oil.

56. The composition of claim 52, wherein x represents the number of recurring units which is ranging between about 50 and about 150 while y represents the number of recurring units which is ranging between 1,000 and about 2,000.

57. The composition of claim 52, wherein the non-volatile solubilising silicone oil of the silicone gum is a phenyltrimethicone of the following formula (II):

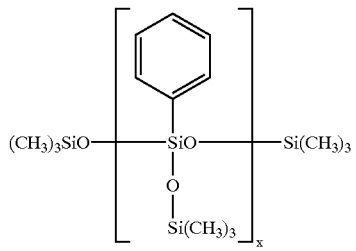

in which x represents the number of recurring units which provides a viscosity between about 10 and about 40 centiStokes at a temperature of 25° C.

58. The composition of claim 57, wherein x has an average value ranging between 2 and 3.

59. A method of cosmetic care comprising applying to skin zones in need thereof a cosmetic composition comprising a fatty phase comprising a diphenyldimethicone silicone gum dissolved in a phenyltrimethicone non-volatile silicone oil, the diphenyldimethicone having the following formula (I):

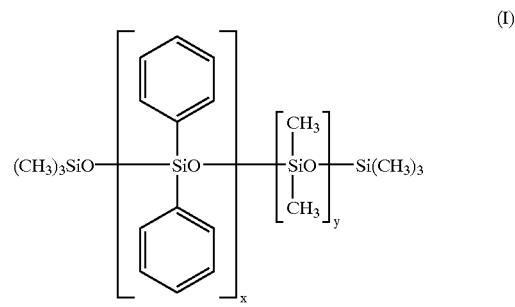

in which x represents the number of recurring units which is less than about 500 while y represents the number of recurring units which is at least equal to 1,000, and wherein the non-volatile solubilising silicone oil of the silicone gum is a phenyltrimethicone of the following formula (II):

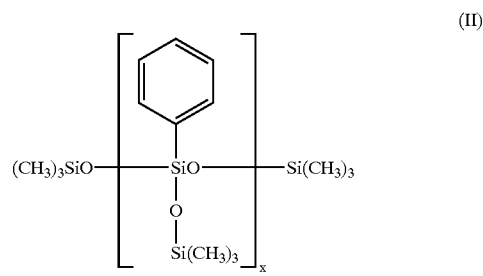

in which x represents the number of recurring units which provides a viscosity between about 10 and about 40 centistokes at a temperature of 25° C.

60. A cosmetic composition having a fatty phase comprising a diphenyldimethicone silicone gum dissolved in a non-volatile phenyltrimethicone silicone oil, the diphenyldimethicone having the following formula (I):

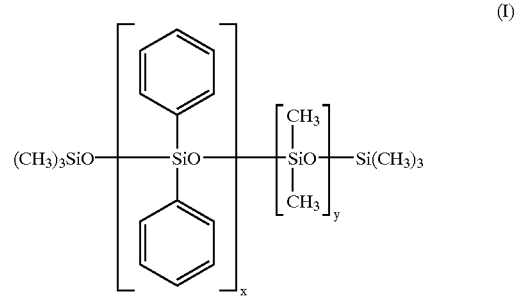

in which x represents the numbers of recurring units which is less than about 500 while y represents the number of recurring units which is at least equal to 1,000, and wherein the non-volatile solubilising silicone oil of the silicone gum is a phenyltrimethicone of the following formula (II):

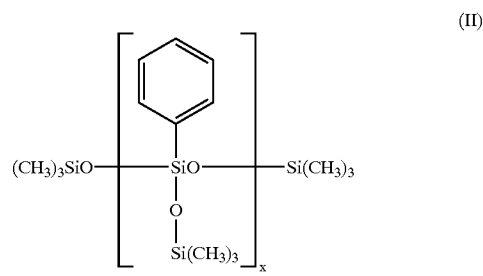

in which x represents the number of recurring units which provides a viscosity between about 10 and about 40 centistokes at a temperature of 25° C.

* * * * *